United States Patent
Yamakage et al.

(10) Patent No.: US 7,926,332 B2
(45) Date of Patent: Apr. 19, 2011

(54) EXHAUST GAS ANALYZER AND EXHAUST GAS ANALYZING METHOD

(75) Inventors: Masahiro Yamakage, Anjo (JP);
Katsutoshi Goto, Okazaki (JP);
Yoshihiro Deguchi, Yokohama (JP);
Kenji Muta, Yokohama (JP); Akio Kondou, Yokohama (JP)

(73) Assignees: Toyota Jidosha Kabushiki Kaisha, Toyota-shi, Aichi-ken (JP); Mitsubishi Heavy Industries, Ltd., Tokyo (JP)

( * ) Notice: Subject to any disclaimer, the term of this patent is extended or adjusted under 35 U.S.C. 154(b) by 189 days.

(21) Appl. No.: 12/159,042

(22) PCT Filed: Dec. 27, 2006

(86) PCT No.: PCT/JP2006/326380
§ 371 (c)(1),
(2), (4) Date: Jun. 24, 2008

(87) PCT Pub. No.: WO2007/077966
PCT Pub. Date: Jul. 12, 2007

(65) Prior Publication Data
US 2009/0229250 A1 Sep. 17, 2009

(30) Foreign Application Priority Data

Dec. 28, 2005 (JP) ................. 2005-379499

(51) Int. Cl.
*G01M 15/10* (2006.01)
(52) U.S. Cl. .................. 73/114.71; 73/23.31
(58) Field of Classification Search ............. 73/114.71, 73/23.31
See application file for complete search history.

(56) References Cited

U.S. PATENT DOCUMENTS
4,432,649 A * 2/1984 Krause ............ 356/438
(Continued)

FOREIGN PATENT DOCUMENTS
JP  3-25352  2/1991
(Continued)

OTHER PUBLICATIONS

M. Yamakage et al., "Development of Direct and Fast Response Gas Measurement," Publication No. 2008-01-0758 (2008).

(Continued)

*Primary Examiner* — Freddie Kirkland, III
(74) *Attorney, Agent, or Firm* — Finnegan, Henderson, Farabow, Garrett & Dunner, LLP

(57) ABSTRACT

An exhaust gas analyzer and an exhaust gas analyzing method capable of analyzing the concentration of particulate matter contained in exhaust gas from an internal combustion in real time are provided. The exhaust gas analyzer includes: an exhaust gas passage hole 21 through which the exhaust gas from the internal combustion is introduced; an optical fiber 25 that applies the laser light in a direction perpendicular to a flow of the exhaust gas flowing through the exhaust gas passage hole; a detector 26 that receives the laser light that has passed through the exhaust gas; a photodetector 71 that receives Mie scattered light generated from particulate matter PM contained in the exhaust gas by irradiating the particulate matter with the laser light; and a personal computer 45 as a calculation unit that calculates a concentration of a component in the exhaust gas based on photoreceiving data of a transmitted light intensity obtained from the detector 26, and calculates a concentration of the particulate matter contained in the exhaust gas based on actual measurement data of a scattered light intensity obtained by the photodetector 71.

8 Claims, 7 Drawing Sheets

U.S. PATENT DOCUMENTS

| | | | |
|---|---|---|---|
| 5,096,834 A * | 3/1992 | Saito | 436/139 |
| 6,542,831 B1 * | 4/2003 | Moosmuller et al. | 702/40 |
| 6,674,528 B2 * | 1/2004 | Adachi et al. | 356/336 |
| 7,041,153 B2 * | 5/2006 | Totoki | 95/3 |
| 7,365,352 B2 * | 4/2008 | Muta et al. | 250/573 |
| 7,650,780 B2 * | 1/2010 | Hall | 73/114.71 |
| 2005/0178675 A1 * | 8/2005 | Hall | 205/775 |
| 2009/0039284 A1 * | 2/2009 | Goto et al. | 250/432 R |
| 2009/0095918 A1 * | 4/2009 | Iwase et al. | 250/432 R |
| 2009/0164138 A1 * | 6/2009 | Goto et al. | 702/24 |
| 2009/0323068 A1 * | 12/2009 | Yamakage et al. | 356/437 |

FOREIGN PATENT DOCUMENTS

| | | | |
|---|---|---|---|
| JP | 3-505131 | | 11/1991 |
| JP | 8-54339 | | 2/1996 |
| JP | 2930710 | | 5/1999 |
| JP | 2000-074830 | * | 3/2000 |
| JP | 2002-48711 | | 2/2002 |
| JP | 2004-117259 | | 4/2004 |
| JP | 2004-264146 | | 9/2004 |
| JP | 2005-23249 | | 1/2005 |
| JP | 2005-24251 | | 1/2005 |
| WO | WO 90/10215 | | 9/1990 |

OTHER PUBLICATIONS

M. Yamakage et al., "Development of Direct and High Response Gas Measurement," Publication No. 20070351 (2007).

M. Yamakage et al., "Development of Direct and High Response Exhaust Gas Measurement (1)," Publication No. 20075153, pp. 21-24 (2007).

Y. Deguchi et al., "Development of Direct and High Response Exhaust Gas Measurement (2)," Publication No. 20075166, pp. 25-28 (2007).

A. Davidy et al., "Development of Inverse Radiative Method for Measuring Gaseous and Particles Concentrations in the Exhaust Plumes by Using Remote Sensing Method," 41$^{st}$ AIAA/ASME/SAE/ASEE Joint Propulsion Conference & Exhibit, AIAA 2005-3577, pp. 1-21 (2005).

H. Kubota et al., "Kogaku Gijutsu Handbook," pp. 1-7 (Apr. 1997).

* cited by examiner

EXHAUST GAS ANALYZER AND EXHAUST GAS ANALYZING METHOD

CROSS-REFERENCE TO RELATED APPLICATIONS

This application is a national phase application of International Application No. PCT/JP2006/326380, filed Dec. 27, 2006, and claims the priority of Japanese Application No. 2005-379499, filed Dec. 28, 2005, the content of both of which is incorporated herein by reference.

TECHNICAL FIELD

The present invention relates to an exhaust gas analyzer and an exhaust gas analyzing method that calculates the concentration of a component contained in exhaust gas emitted from an internal combustion of an automobile or the like, and calculates the concentration of particulate matter contained in the exhaust gas.

BACKGROUND ART

Conventionally, methods and apparatuses for measuring various components contained in exhaust gas emitted from an internal combustion of an automobile or the like have been already proposed. For instance, Patent Document 1 discloses a vehicle capable of mounting a NDIR (non-dispersive infrared spectroscopy) gas analyzer, an exhaust gas flowmeter and an arithmetic processing circuit, the NDIR gas analyzer for continuously measuring the HC (hydrocarbon) concentration in exhaust gas flowing through an exhaust tube connected with an engine, the exhaust gas flowmeter continuously measuring a flow rate of the exhaust gas flowing through the exhaust tube, and the arithmetic processing circuit performing arithmetic processing of an output from the NDIR gas analyzer and an output from the exhaust gas flowmeter to continuously calculate the THC (total hydrocarbon) amount in the exhaust gas, thus enabling the measurement of the HC concentration contained in the exhaust gas from the internal combustion of a vehicle such as an automobile traveling on a road. Patent Document 1, however, does not refer to the measurement of particulate matter contained in the exhaust gas.

Patent Document 2 describes a laser measurement apparatus capable of measuring the concentration of suspended particulate matter contained in exhaust gas from an automobile or the like as well as the concentration of carbon dioxide, nitrogen oxides or the like contained in the exhaust gas. In this case, the exhaust gas is introduced into a sampling tube, at one side of which a laser light source is placed and at the other side of which a photoreceiver is placed, so that the applied laser light is scattered by the particulate matter suspended in the exhaust gas, and the thus attenuated laser light is received by the photoreceiver side, thus measuring the concentration of the particulate matter from the attenuation.

Patent Document 1: JP Published Patent Application No. 2004-117259 A

Patent Document 2: JP Published Patent Application No. 2002-48711 A

DISCLOSURE OF THE INVENTION

Problem to be Solved by the Invention

From the environmental viewpoint, it becomes a significant challenge to determine quantitatively particulate matter contained in exhaust gas emitted from an internal combustion of an automobile or the like with accuracy, including carbon minute particles, sulfur minute particles such as sulfate, high molecular weight hydrocarbon minute particles (SOF) and the like. The method described in Patent Document 2 that uses information resulting from the scattered light of the laser light to calculate (measure) the concentration of the particulate matter in the gas is expected as an effective countermeasure therefor.

However, the following problem will arise when the laser measurement apparatus using infrared laser light described in Patent Document 2 is applied to an exhaust gas tube. That is, when particles to be measured have different particle diameters, a signal intensity and a particle concentration will not have a proportional relationship, thus degrading the measurement accuracy. In order to improve the measurement accuracy, light of a plurality of wavelengths has to be used, which makes the apparatus complicated. Moreover, when a component concentration, a temperature and particulate matter are to be measured at one time, a plurality of apparatuses have to be combined, causing an increase in size and cost of the apparatus.

In view of the above-stated problems, it is an object of the invention to provide an exhaust gas analyzer and an exhaust gas analyzing method capable of calculating the concentration of particulate matter contained in exhaust gas emitted from an internal combustion of an automobile or the like using laser light for analyzing the concentration of a component contained in the exhaust gas, thus enabling simultaneous calculation of the component analysis in the exhaust gas and the measurement of the particulate matter contained in the exhaust gas with accuracy.

Means for Solving the Problem

In order to fulfill the above-stated object, an exhaust gas analyzer of the present invention analyzes exhaust gas emitted from an internal combustion by irradiating the exhaust gas with laser light, and the exhaust gas analyzer includes: an inlet through which the exhaust gas is introduced; a light irradiation unit that applies the laser light in a direction perpendicular to a flow of the exhaust gas flowing through the inlet; a transmitted light photoreceiving unit that receives the laser light that has passed through the exhaust gas; a scattered light photoreceiving unit that receives Mie scattered light generated from particulate matter contained in the exhaust gas by irradiating the particulate matter with the laser light; and a calculation unit that calculates a concentration of a component in the exhaust gas based on photoreceiving data of a transmitted light intensity obtained from the transmitted light photoreceiving unit, and calculates a concentration of the particulate matter contained in the exhaust gas based on actual measurement data of a scattered light intensity obtained by the scattered light photoreceiving unit.

A method for analyzing exhaust gas of the present invention is for analyzing the exhaust gas emitted from an internal combustion by irradiating the exhaust gas with laser light. The method includes the steps of: irradiating the exhaust gas with the laser light, receiving the laser light that has passed through the exhaust gas, and calculating a concentration of a component contained in the exhaust gas based on the received laser light; and receiving Mie scattered light generated from particulate matter contained in the exhaust gas by irradiating the particulate matter with the laser light, and calculating a concentration of the particulate matter in the exhaust gas based on actual measurement data of an intensity of the received Mie scattered light and a theoretical value data about Mie scattered light specified for each particle diameter.

According to the exhaust gas analyzer and the exhaust gas analyzing method of the present invention, basically, exhaust gas is irradiated with laser light, the laser light that has passed through the exhaust gas is received, and the concentration of a component contained in the exhaust gas is calculated based on the received laser light, while calculating the concentration of particulate matter by receiving Mie scattered light generated from the particulate matter by the irradiation with the laser light. Then, the concentration of the particulate matter is measured based on the facts that when particulate matter of a certain particle diameter is irradiated with laser light, the intensity of Mie scattered light generated therefrom has wavelength dependency of the laser light applied, and letting that the wavelength is on the horizontal axis and the Mie scattered light intensity is on the vertical axis, a theoretical value pattern will be drawn that is specific to the particle diameter, and that the specific theoretical value pattern varies depending on the particle diameter.

The exhaust gas emitted from an internal combustion from an automobile or the like will vary in the component concentration or in the particulate matter concentration depending on the operational environment of the internal combustion. Further, the particulate matter of different particle diameters mixed therein is emitted. In the present invention, a light source capable of applying laser light of a plurality of wavelengths is placed at the inlet, through which the exhaust gas from the internal combustion is introduced, and laser light of the plurality of wavelengths is applied to the exhaust gas flowing therethrough. The applied laser light is incident on particulate matter contained in the exhaust gas to be scattered, and Mie scattered light is generated with a necessary intensity for each wavelength. The thus generated Mie scattered light is received by the scattered light photoreceiving unit and the received data is sent to the calculation unit as actual measurement data of the Mie scattered light intensity for each wavelength.

As described above, the particulate matter of different particle diameters mix in the exhaust gas, and such particulate matter will generate Mie scattered light of different intensities. However, it can be considered that the actual measurement data of the Mie scattered light intensity for each wavelength received by the scattered light photoreceiving unit will substantially agree with the Mie scattered light intensity data from the particulate matter of the dominant particle diameter.

The actual measurement data of the Mie scattered light intensity for each wavelength that is actually measured is compared with the theoretical value data about the Mie scattered light intensities stored in the data storage unit and specified for each particle diameter, so as to select the closest theoretical value pattern data as a pattern (pattern matching). Based on the selected theoretical value pattern data, the dominant particle diameter in the particulate matter contained in the exhaust gas measured can be estimated.

From the selected theoretical value pattern data, the maximum value of the Mie scattered light intensity is obtained, and then the calculation unit calculates a concentration as a theoretical value from the relationship between the Mie scattered light intensity and the concentration based on the Mie scattering theory. The calculation unit further corrects the concentration of the particulate matter that is the calculated theoretical value data with the measurement value of the Mie scattered light intensity that is actually measured by a conveniently known method. Thereby, an actual particulate matter concentration in the measured exhaust gas can be obtained (for example, mg/m3 or %). The correction method includes determining based on the actual measurement result or using a coefficient determined from a theoretical formula about the Mie scattered light. In either case, laser light of predetermined wavelengths is actually applied to particulate matter of a known particle diameter flowing through for the verification beforehand, whereby the concentration can be calculated with higher accuracy.

As described above, according to the exhaust gas analyzer and the exhaust gas analyzing method of the present invention, the concentration of the particulate matter contained in the exhaust gas is calculated using the particle diameter of the particulate matter as one calculation basis, thus enabling the calculation with accuracy.

In the exhaust gas analyzer of the present invention, preferably, the calculation unit includes a data storage unit that stores theoretical value data about a Mie scattered light intensity specified for each particle diameter. The calculation unit calculates the concentration of the particulate matter contained in the exhaust gas based on the actual measurement data of a scattered light intensity obtained by the scattered light photoreceiving unit and the theoretical value data stored in the data storage unit.

According to the thus configured exhaust gas analyzer, the actual measurement data and the theoretical value data are compared, and the theoretical value pattern data that is the closest as a pattern is selected. Then, the particle diameter of the particulate matter contained in the exhaust gas is estimated based on the selected theoretical value data, and the concentration of the particulate matter is calculated based on the estimated particle diameter, and therefore the concentration of the particulate matter can be calculated with higher accuracy.

The exhaust gas analyzer of the present invention preferably includes a plurality of the scattered light photoreceiving units, and the calculation unit further includes means that calculates an average of actual measurement data of Mie scattered light intensities obtained by the plurality of scattered light photoreceiving units. In this case, the actual measurement value of the Mie scattered light intensity data for each wavelength can be obtained as the average of the plurality of actual measurement values, and therefore theoretical value pattern data can be selected (pattern matching) with higher accuracy.

EFFECTS OF THE INVENTION

According to the present invention, it is possible to calculate the concentration of particulate matter in exhaust gas emitted from an internal combustion of an automobile or the like with accuracy as well as a concentration, a temperature, a pressure and the like of a component contained in the exhaust gas.

Figure 1:
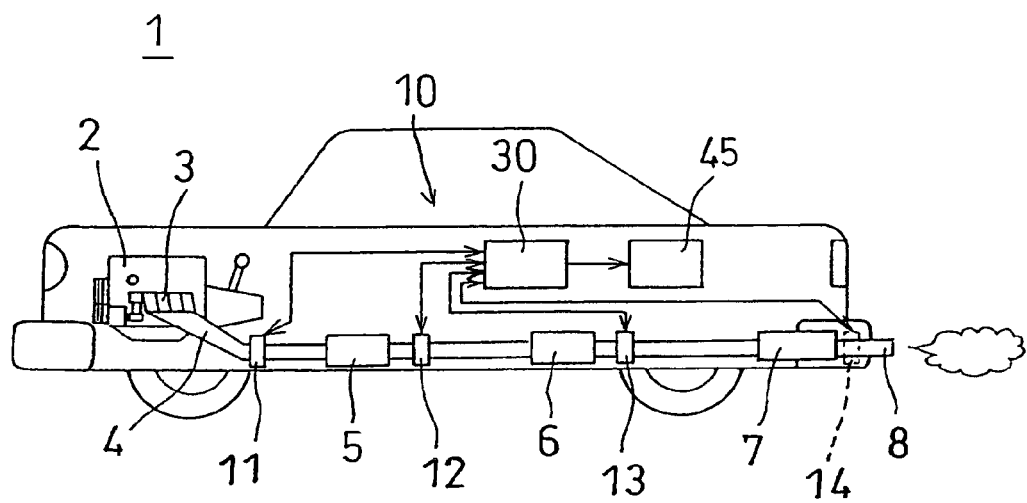
FIG. 1 illustrates the configuration of major parts in one embodiment where an exhaust gas analyzer according to the present invention is mounted in a vehicle.

In these drawings, the respective reference numbers denote the followings:

1 automobile
1A engine bench
2 engine (internal combustion)
3 exhaust manifold (exhaust path)
4 exhaust tube (exhaust path)
5 first catalyst device (exhaust path)
6 second catalyst device (exhaust path)
7 muffler (exhaust path)
8 exhaust pipe (exhaust path)
10 exhaust gas analyzer (gas analyzer)
11 to 14 sensor unit
20 sensor base
21 exhaust gas passage hole (inlet)
23 sensor hole (irradiated light passage hole)
24 sensor hole (transmitted light passage hole)
25 optical fiber (irradiation unit)
26 detector (photoreceiving unit)
28, 29 mirror
38 light passage hole
30 laser oscillation/photoreceiving controller
33 demultiplexer
34A to 34C demultiplexer
35A to 35C multiplexer
36A to 36C multiplexer
40A to 40C differential photodetector
45 personal computer (signal analyzer)
46 storage unit
47 calculation unit
70, 70a third sensor hole
71, 71a Mie scattered light photodetector
R(Ra) laser light
S Mie scattered light
PM particulate matter

BEST MODE FOR CARRYING OUT THE INVENTION

Figure 2:
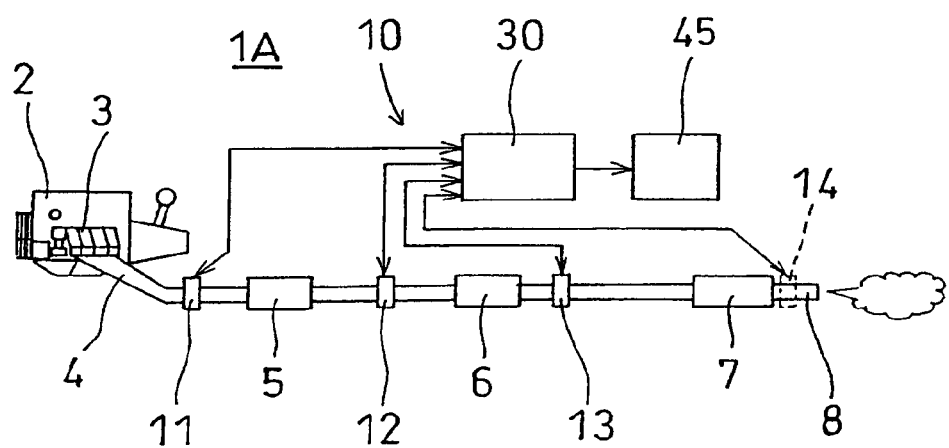
FIG. 2 illustrates the configuration of major parts in another embodiment where the exhaust gas analyzer according to the present invention is mounted in an engine bench.
Figure 3:
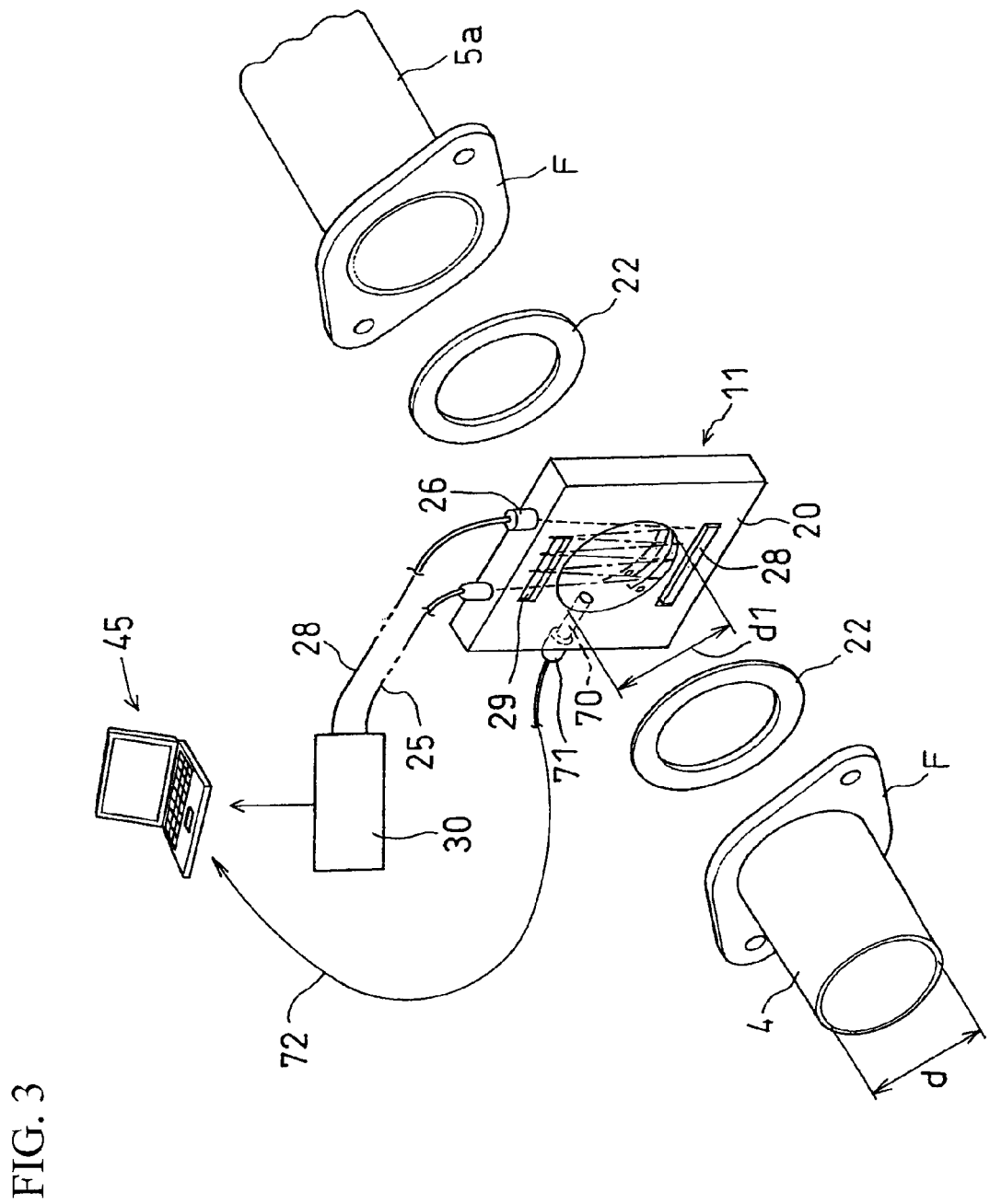
FIG. 3 illustrates the configuration of major parts of an exhaust gas analyzer, including a perspective view of a disassembled state of major parts of one sensor unit.
Figure 4:
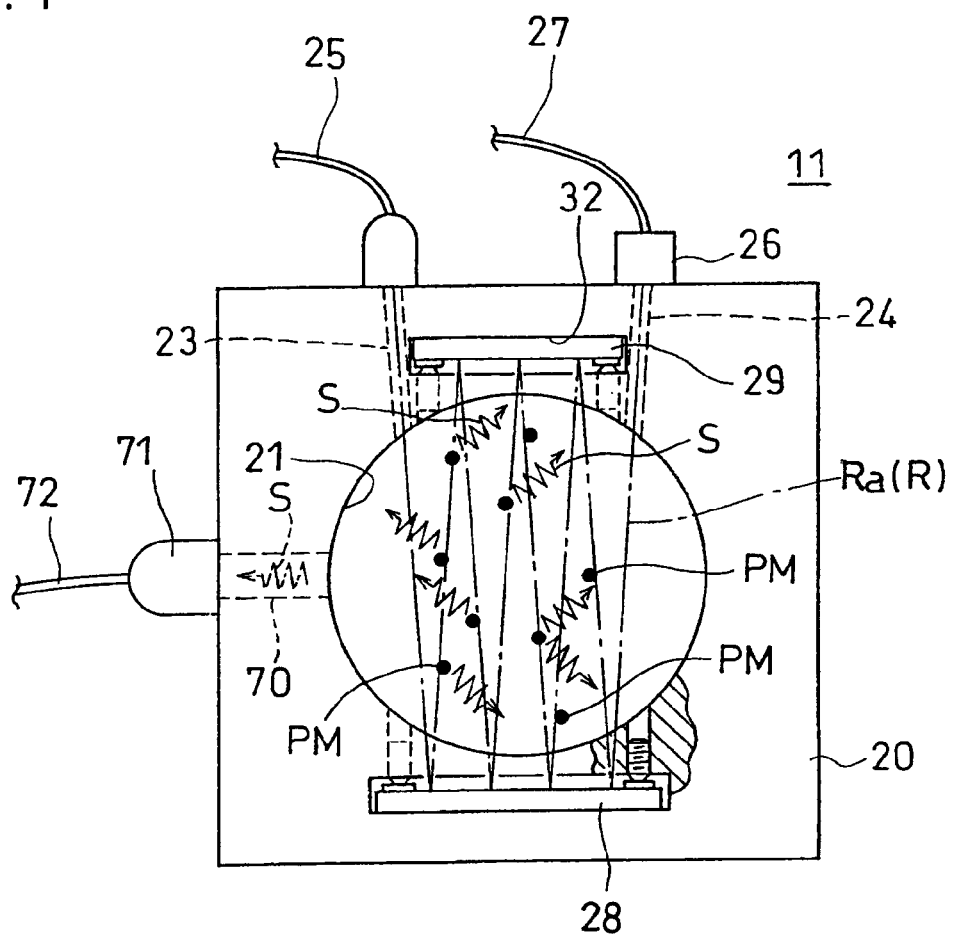
FIG. 4 is a front view of the sensor unit of FIG. 3.
Figure 5:
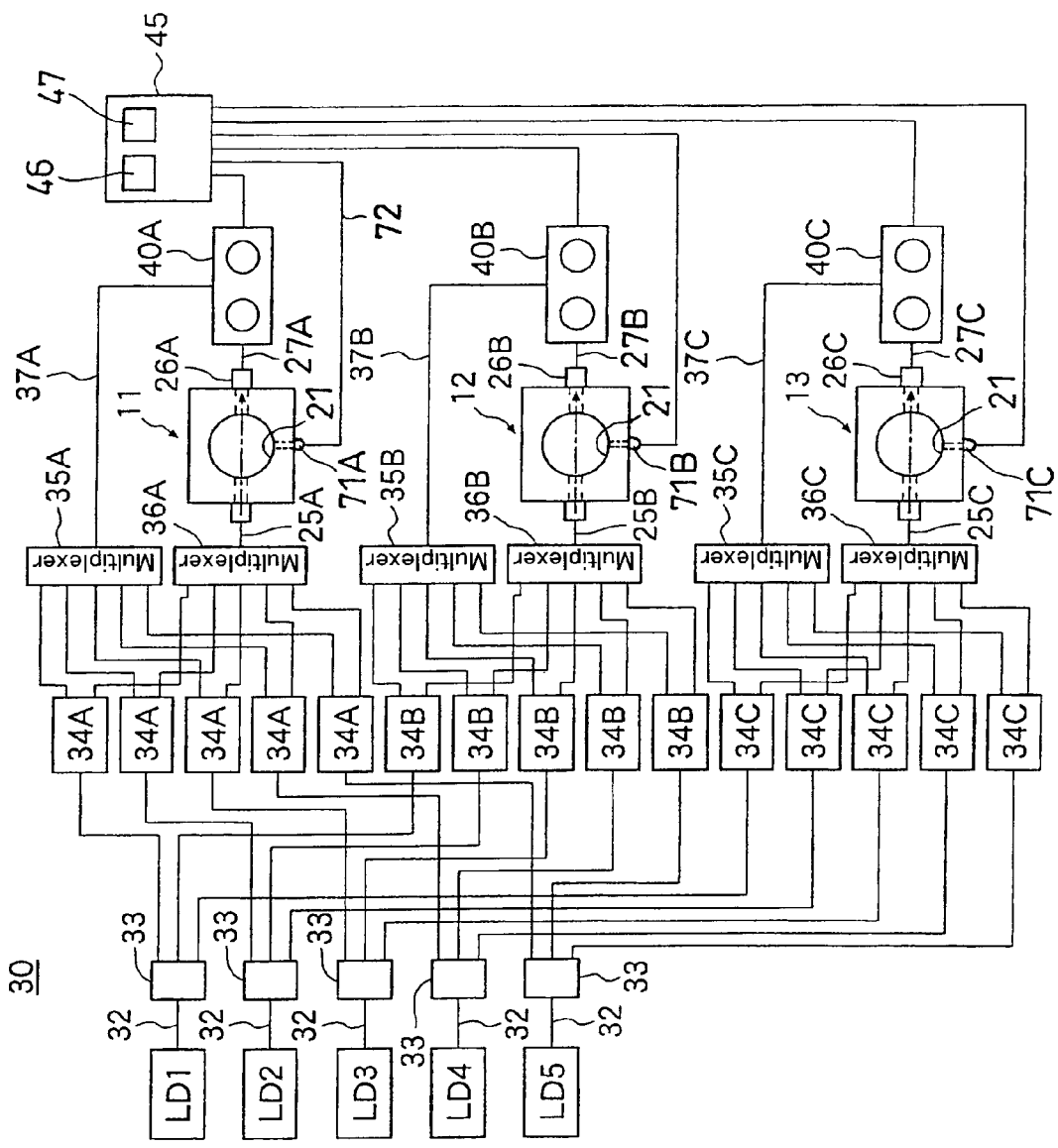
FIG. 5 is a block diagram illustrating the overall configuration of the exhaust gas analyzer, including the configuration of major parts of a laser oscillation/photoreceiving controller and a signal analyzer FIG. 6 explains that when laser light of different wavelengths is applied to particulate matter of a certain particle diameter, the Mie scattered light intensity generated therefrom draws a certain pattern with respect to the wavelengths.

The following is a detailed description of one embodiment in which an exhaust gas analyzer according to the present invention is used as an analyzer for exhaust gas from an internal combustion (engine) of an automobile, with reference to the drawings. FIG. 1 illustrates the configuration of major parts of the exhaust gas analyzer according to the present embodiment mounted in an automobile; FIG. 2 illustrates the configuration of major parts of the exhaust gas analyzer of FIG. 1 mounted in an engine bench; FIG. 3 is a perspective view illustrating a disassembled state of a sensor unit and the vicinity thereof; and FIG. 4 illustrates the details of the sensor unit. FIG. 5 is a block diagram illustrating the overall configuration of the exhaust gas analyzer including the configuration of major parts of a laser oscillation/photoreceiving controller and a signal analyzer.

In FIGS. 1 to 3, the exhaust gas analyzer of the present embodiment is an apparatus that analyzes exhaust gas emitted from an internal combustion (engine) 2 installed in an automobile 1. As shown in FIG. 2, it may be an apparatus that analyzes exhaust gas emitted from an internal combustion (engine) 2 installed in an engine bench 1A. The exhaust gas emitted from each cylinder of the engine 2 joins together in an exhaust manifold 3, is directed into a first catalyst device 5 through an exhaust tube 4, is further directed into a second catalyst device 6, and is then discharged through an exhaust pipe 8 via a muffler 7 to the atmosphere. The exhaust manifold 3, the exhaust tube 4, the first catalyst device 5, the second catalyst device 6, the muffler 7 and the exhaust pipe 8 make up an exhaust path, so that the exhaust gas emitted from the engine 2 undergoes the purification by the two catalyst devices 5 and 6 and the sound reduction and the pressure reduction by the muffler 7 to be discharged to the atmosphere. The muffler may include two parts of a main muffler and a sub-muffler.

The plurality of components making up the exhaust path are connected with each other by letting the respective flange portions opposed to and in contact with each other and fastening them with a bolt or the like. For instance, the first and the second catalyst devices 5 and 6 each have exhaust pipe portions connected to the upstream and downstream sides of their main bodies having larger diameters, and flange portions F, F are fixedly attached to the ends of the exhaust pipe portions by welding, for example. The muffler 7 has exhaust pipe portions connected to the upstream and downstream sides of its main body having a larger diameter, and flange portions F, F are fixedly attached to the ends of the exhaust pipe portions. The exhaust pipe 8 at the end is fixedly attached directly to the muffler 7 by welding, for example. Thus, the plurality of components making up the exhaust path are connected via the flange portions F, and the exhaust path, through which exhaust gas passes, is formed to be circular in cross section with a diameter of d.

The exhaust gas analyzer 10 of the present embodiment includes a plurality of sensor units (four units in the illustrated example) 11 to 14 disposed at a plurality of locations along the exhaust path. A first sensor unit 11 is disposed between the first catalyst device 5 and the upstream exhaust tube 4 on the engine side. A second sensor unit 12 is disposed downstream of the first catalyst device 5. A third sensor unit 13 is disposed downstream of the second catalyst device 6. A fourth sensor unit 14 is installed in the exhaust pipe 8 downstream of the muffler 7. The sensor unit 14 may be disposed partway through the exhaust pipe or may be inserted in the exhaust pipe at the open end thereof. Another sensor unit may be installed at an exhaust tube for each cylinder upstream of the first sensor unit 11 before the exhaust gas joins together at the exhaust manifold 3.

The exhaust tube 4, the first catalyst device 5, the second catalyst device 6, and the muffler 7 are coupled by fastening the flange portions F, F with bolts. The sensor units 11, 12, and 13 disposed between the components making up the exhaust path are disposed while each being sandwiched by the flange portions F, F. The flange portions F, F are formed at both ends of each component making up the exhaust path, and the joint plane of the flange portions intersects perpendicularly the center line of the exhaust path. As a result, the sensor units 11 to 13 are disposed to traverse the exhaust path while being sandwiched by the flange portions F, F. The fourth sensor unit 14, which analyzes the exhaust gas immediately before it is emitted to the atmosphere, may be disposed at an intermediate point of the exhaust pipe 8 protruding from the muffler 7 while being sandwiched between the flange portions F, F. Any number of such sensor units may be disposed.

Since the respective sensor units 11 to 14 have identical configurations; the following describes one of them, the sensor unit 11, with reference to FIGS. 3 and 4. The sensor unit 11 includes a sensor base 20 formed of a rectangular thin plate, at a center portion of which an exhaust gas passage hole 21 is formed having a diameter dl which is approximately the same as the inner diameter d of the circular cross section of the exhaust pipe portion, through which the exhaust gas passes. The exhaust gas passage hole 21 makes up an inlet of the exhaust gas. The plate-shaped sensor base 20 has such a thickness as to enable the fixing of a laser light irradiation unit and a photoreceiving unit (including both of a transmitted light photoreceiving unit and a scattered light photoreceiving unit described later), which is, however, desirably as small as possible.

More specifically, the thickness of the sensor base 20 is preferably about 5 to 20 mm, for example. A thickness more than 20 mm tends to cause disturbance in the exhaust gas flow, or tends to generate considerable pressure loss. A thickness less than 5 mm will make the installation of the irradiation unit or the photoreceiving unit of the laser unit for measurement complicated. The diameter dl of the exhaust gas passage hole 21 is desirably the same as the inner diameter d of the circular cross section of the exhaust pipe portion. In this respect, however, when the inner diameter d of the circular cross section of the exhaust pipe portion is 30 mm, the diameter dl of the exhaust gas passage hole 21 of around 30±1 to 2 mm, for example, will be within a permissible error range. The sensor base 20 may be formed of a metal or ceramics plate; which is not particularly limited.

The sensor base 20 is fixed while being sandwiched between flange portions F, F, with a gasket 22 disposed between each flange portion F and the sensor base 20, which are then fastened with bolts and nuts not illustrated, for example. The gaskets 22 are formed of appropriate material, and have an exhaust gas passage hole bored therein with the same diameter as the inner diameter of the exhaust pipe portion. This structure prevents the leakage of exhaust gas even when the sensor base 20 is inserted between the flange portions F, F for the connection of the exhaust path, without much increase in the exhaust path length. FIG. 3 illustrates a configuration in which the sensor base 20 is fixed between the flange portion F welded to the downstream end of the exhaust tube 4 and the flange portion F welded to the end of the exhaust pipe portion 5a upstream of the catalyst device 5, via gaskets 22, 22.

The sensor base 20 has first and second sensor holes 23 and 24 formed so as to penetrate through a center of the thickness of the plate from an edge surface toward the exhaust gas passage hole 21. The sensor base 20 also has a third sensor hole 70, which penetrates from another edge surface different from the edge face with the first and the second sensor holes 23 and 24 formed similarly to the exhaust gas passage hole 21. The cross section of the third sensor hole 70 is set larger than the cross sections of the first and the second sensor holes 23 and 24.

As described later, the first sensor hole 23 is a passage hole for laser light R that is applied to the exhaust gas passage hole 21, at which an optical fiber 25 is fixed as an irradiation unit from which the laser light R is applied. A second sensor hole 24 is a passage hole for attenuated laser light Ra that has passed through the exhaust gas, and at the exit side of the laser light in the second sensor hole 24 a detector 26 is provided as the transmitted light photoreceiving unit. The third sensor hole 70 serves as a passage hole for Mie scattering light S that is generated when particulate matter PM contained in the exhaust gas is irradiated with the laser light, and on the side of the third sensor hole 70 opposite to the exhaust gas passage hole 21, an appropriate photodetector 71 is provided as a Mie scattered light photoreceiving unit. Preferably, the first and the second sensor holes 23 and 24 and the third sensor hole 70 are bored in the direction perpendicular to the flowing direction of the exhaust gas.

Incidentally, in the case where the exhaust gas analyzer of the present invention is used only for the concentration analysis of the particulate matter PM in the measured exhaust gas, the above-described detector 26 as the transmitted light photoreceiving unit may not be operated, and instead laser light is applied from the optical fiber 25 and Mie scattered light generated from the particulate matter PM may be received by the photodetector 71 via the third sensor hole 70.

In the illustrated example, as shown in FIG. 4, two mirrors 28 and 29 are disposed outside the exhaust gas passage hole 21 and at opposing positions with the exhaust gas passage hole 21 sandwiched therebetween so that the reflecting faces of the mirrors are parallel to each other. The laser light entering through the first sensor hole 23 is reflected by the two mirrors 28 and 29, and is attenuated while passing through the exhaust gas. As mentioned earlier, the attenuated laser light Ra passes through the second sensor hole 24 to be received by the detector 26. During the passage through the exhaust gas passage hole 21 while being reflected, if the exhaust gas contains particulate matter PM, Mie scattered light S is generated with an amount depending on the particle diameter and the concentration thereof. The generated Mie scattered light S passes through the third sensor hole 70 to be detected by the photodetector 71 as described above.

Mirrors 28 and 29 are manufactured by coating a reflecting member on a surface of a base member made of quartz, sapphire, ceramic or the like. As the coating member, a material with a high reflectivity such as gold, platinum, or titanium oxide matching with a laser wavelength is preferably selected. In order to protect the reflecting member, a material such as $MgF_2$ or $SiO_2$ that is clear and has excellent heat resistance and environmental resistance is preferably formed as a coating layer at the uppermost face thereof. The use of a mirror with excellent heat resistance and a high reflectively enables the accurate measurement. On the surface of each mirror 28, 29, a photocatalytic layer such as a titanium dioxide ($TiO_2$) layer may be formed.

A method for calculating the concentration of the particulate matter PM contained in the exhaust gas according to the present invention is principally based on the fact that, when particulate matter of a certain particle diameter is irradiated with laser light, the intensity of Mie scattered light generated therefrom has wavelength dependency of the laser light applied, and letting that the wavelength is on the horizontal axis and the Mie scattered light intensity is on the vertical axis, a theoretical value pattern will be drawn that is specific to the particle diameter. To this end, laser light of a plurality of wavelengths has to be applied from the optical fiber 25 to the exhaust gas passage hole 21, through which the exhaust gas flows. Further, the Mie scattered light detection side has to detect the wavelength-dependent Mie scattered light intensity for each wavelength.

FIG. 5 illustrates an exemplary laser oscillation/photoreceiving controller 30 for that purpose. In the illustrated example of FIG. 5, infrared laser light of a plurality of wavelengths emitted from the laser oscillation/photoreceiving controller 30 is applied to the exhaust gas passage hole 21 in the sensor base 20 via an optical fiber 25A (25B, 25C), and the infrared laser light that has passed through the exhaust gas is received by a detector 26A (26B, 26C) on the transmitted light photoreceiving side. A differential photodetector 40A (40B, 40C) compares the measured light with signal light, and a differential signal is supplied to a personal computer 45 as an analyzer, where the components of the exhaust gas are analyzed. Meanwhile, the Mie scattered light S generated in the exhaust gas passage hole 21 by the irradiation with the laser light is detected by a photodetector 71A (71B, 71C), and the information thereon is transmitted to the personal computer 45 via a signal line 72, where the concentration of the particulate matter PM is calculated as described later.

More specifically, as shown in FIG. 5, the laser oscillation/photoreceiving controller 30 includes a plurality of laser diodes LD1 to LD5, to each of which a frequency signal is supplied from a signal generator such as a function generator (not illustrated). Then, each laser diode LD1 to LD 5 emits infrared laser light with a wavelength band corresponding to the frequency. It is effective for the infrared laser light passing through the exhaust gas to have a peak wavelength corresponding to an absorbing spectrum specific to each component in the exhaust gas detected. For instance, when carbon monoxide (CO), carbon dioxide ($CO_2$), ammonia ($NH_3$), methane ($CH_4$), and water ($H_2O$) are to be detected, infrared laser light of five wavelengths is used. For example, the wavelength suitable for the detection of ammonia is 1530 nm, the wavelength suitable for the detection of carbon monoxide is 1460 nm, and the wavelength suitable for the detection of carbon dioxide is 1470 nm. The wavelength suitable for the detection of methane is 1680 nm, and the wavelength suitable for the detection of water is 1350 nm. Different wavelengths may be applied to the detection of gas concentration of the same component, and therefore one may be selected among the different wavelengths for use.

The infrared laser light applied from each of the laser diodes LD1 to LD5 is guided by an optical fiber 32 to a first demultiplexer 33, where the light is demultiplexed in accordance with the number of the sensor units. The laser light thus demultiplexed by the first demultiplexer 33 is separated into signal light and measurement light by second demultiplexers 34A (34B, 34C). The second demultiplexers 34A are for the sensor unit 11; the second demultiplexers 34B are for the sensor unit 12; and the second demultiplexers 34C are for the sensor unit 13.

The signal light of each wavelength band separated by the five second demultiplexers 34A (34B, 34C) for the sensor unit 11 (12, 13) passes through optical fibers and is multiplexed by a multiplexer 35A (35A, 35C). The multiplexed signal light of a plurality of wavelength bands is then guided via an optical fiber 37A (37B, 37C) to the above-mentioned differential photodetector 40A (40B, 40C). Meanwhile, the measurement light separated by the five second demultiplexers 34A passes through optical fibers and is multiplexed by a multiplexer 36A (36B, 36C), and the multiplexed light is then guided to the irradiation unit of the sensor unit 11 (12, 13) via the optical fiber 25A (25B, 0.25c).

The laser light for measurement from the irradiation light passes through the exhaust gas passage hole 21 while being reflected by the mirrors 28 and 29 as shown in FIG. 4, and the attenuated transmitted laser light Ra that has passed through the exhaust gas is detected by the detector 26A (26B, 26C) as photoreceiving data. The detected signal is transmitted via a signal line 27A (27B, 27C) to the above-mentioned differential photodetector 40A (40B, 40C). The differential photodetector 40A (40B, 40C) is configured to find a difference between the attenuated transmitted light that has passed through the exhaust gas (measurement light) and signal light that does not pass through the exhaust gas, and an electrical signal corresponding to the difference between the signal light and the measurement light calculated by the differential photodetector 40 is amplified by a preamplifier (not shown), for example, and the amplified signal is input via an A/D converter to the personal computer 45 as a signal analyzer. The personal computer 45 calculates the concentration of components contained in the exhaust gas, and the temperature and the pressure of the exhaust gas, for example, from the input signal, so as to analyze the components in the exhaust gas.

In the exhaust gas analyzer 10 of the present invention, infrared laser light, for example, is allowed to pass through the exhaust gas, and the concentration of an exhaust gas component is calculated based on the intensity of the incident light and the intensity of the transmitted light that has passed through the exhaust gas, so as to analyze the exhaust gas. That is, concentration C of an exhaust gas component is calculated from the following equation (1):

$$C = -ln(I/I_0)/kL \tag{1}$$

In the equation (1), I is the transmitted light intensity, $I_0$ is the incident light intensity, k is absorptance, and L is the transmission distance. Thus, concentration C of an exhaust gas component is calculated based on the ratio of transmitted light intensity (I) to incident light intensity ($I_0$) as signal light, i.e., based on the signal intensity ($I/I_0$). The transmitted light intensity I is output via the detector 26A (26B, 26C), and the incident light intensity $I_0$ is output via the optical fiber 37A (37B, 37C) from a photoelectric converter, such as a photodiode in the differential photodetector 40A (40B, 40C) via the optical fiber 37A (37B, 37C). In the present embodiment, the intensity of the signal light that does not pass through the exhaust gas is used as the incident light intensity $I_0$.

The operation of the thus configured exhaust gas analyzer 10 of the present embodiment is described in the following. While the engine is operated, the exhaust gas analyzer 10 is activated. The exhaust gas emitted from the engine 2 joins together in the exhaust manifold 3 of the exhaust path, is directed into the first catalyst device 5 through the exhaust tube 4, is further directed into the second catalyst device 6, and is then discharged through the exhaust pipe 8 via the muffler 7 to the atmosphere. The exhaust gas passes through the exhaust gas passage hole 21 formed in the sensor base 20 of each of the sensor units 11 to 14 disposed along the exhaust path. When the concentration or the like of a specific component in the exhaust is to be measured, laser light is applied to the exhaust gas passage hole 21, and the intensity of the laser light that has passed through the exhaust gas is measured.

That is, the signal generator of the laser oscillation/photoreceiving controller 30 is activated so as to supply a signal to each of the laser diodes LD1 to LD5, thus making each of the laser diodes LD1 to LD5 emit infrared laser light of a predetermined wavelength. The infrared laser light emitted from each of the laser diodes LD1 to LD5 passes through the optical fiber 32 . . . to the demultiplexer 33 . . . , where the light is demultiplexed in accordance with the number of the sensor units. Thereafter, the laser light thus demultiplexed is separated into signal light and measurement light by demultiplexers 34A . . . , 34B . . . , 34C . . . .

One sensor unit 11 is described below in detail. The signal light demultiplexed by the five demultiplexers 34A is multiplexed by the multiplexer 35A to be laser light for signal, which is then guided to the differential photodetector 40A. Meanwhile, the measurement light separated by the five demultiplexers 34A is multiplexed by a multiplexer 36A to be laser light for measurement, which is then guided to the irradiation unit of the sensor unit 11 via the optical fiber 25A. The same goes for other sensor units 12 and 13, i.e., the infrared laser light is demultiplexed by the demultiplexers 33 . . . , followed by demultiplexing by the demultiplexers 34B . . . , 34C . . . , into signal light and measurement light. The signal light is multiplexed by the multiplexers 35B . . . , 35C . . . , and is guided to the differential photodetectors 40B, 40C, whereas the measurement light is multiplexed by the multiplexers 36B, 36C, and is guided to the sensor units 12, 13.

Then, the infrared laser light for measurement applied from the optical fiber 25A (25B, 25C) of each of the sensor unit 11 to 13 passes through the sensor hole 23 as the irradiated light passage hole and is applied to the exhaust gas passage hole 21 through which the exhaust gas passes. The infrared laser light traverses the exhaust gas passage hole 21 of the exhaust path, reaches the mirror 28 via a light passage hole to be reflected upward by the lower mirror 28, and then reaches the mirror 29 via a light passage hole to be reflected downward by the upper mirror 29. The thus repeated reflection increases the transmission distance in the exhaust gas, and finally the light is received by the detector 26A (26B, 26C) via the sensor hole 24. That is, the infrared laser light for measurement is attenuated by the passage through the exhaust gas, and the thus attenuated transmitted light is received by the detector as the photoreceiving unit, so that the light intensity of the transmitted light (measurement light) is measured.

The infrared laser light for measurement that is attenuated through the exhaust gas to reach the photoreceiving unit is output by the detector 26A (26B, 26C) as an electrical signal, and the output signal is supplied via the signal line 27A (27B, 27C) to the differential photodetector 40A (40B, 40C). Meanwhile, the laser light for signal is supplied via the optical fiber 37A (37B, 37C) to the differential photodetector 40A (40B, 40C), and the differential photodetector finds a difference between the transmitted light (measurement light) and the signal light for each of a plurality of wavelength components, thus detecting an absorbing spectrum by which a peak wavelength specific to a certain gas component among the transmitted light is detected. Thus, the output from the differential photodetector is input to the personal computer 45 as a signal analyzer. The personal computer 45 calculates and measures, based on the peak wavelength for each of the plurality of frequency bands of the input absorbing spectra, the concentration of components contained in the exhaust gas, and the temperature and the pressure of the exhaust gas for analysis.

In the exhaust gas analyzer 10 of the present embodiment, when particulate matter PM is present in the exhaust gas, Mie scattered light S will be generated by irradiating the particulate matter PM with the measurement light. Referring now to the flowchart of FIG. 7, a method for calculating the concentration of the particulate matter PM in the exhaust gas to be measured using the generated Mie scattered light S intensity will be described below.

Figure 6:
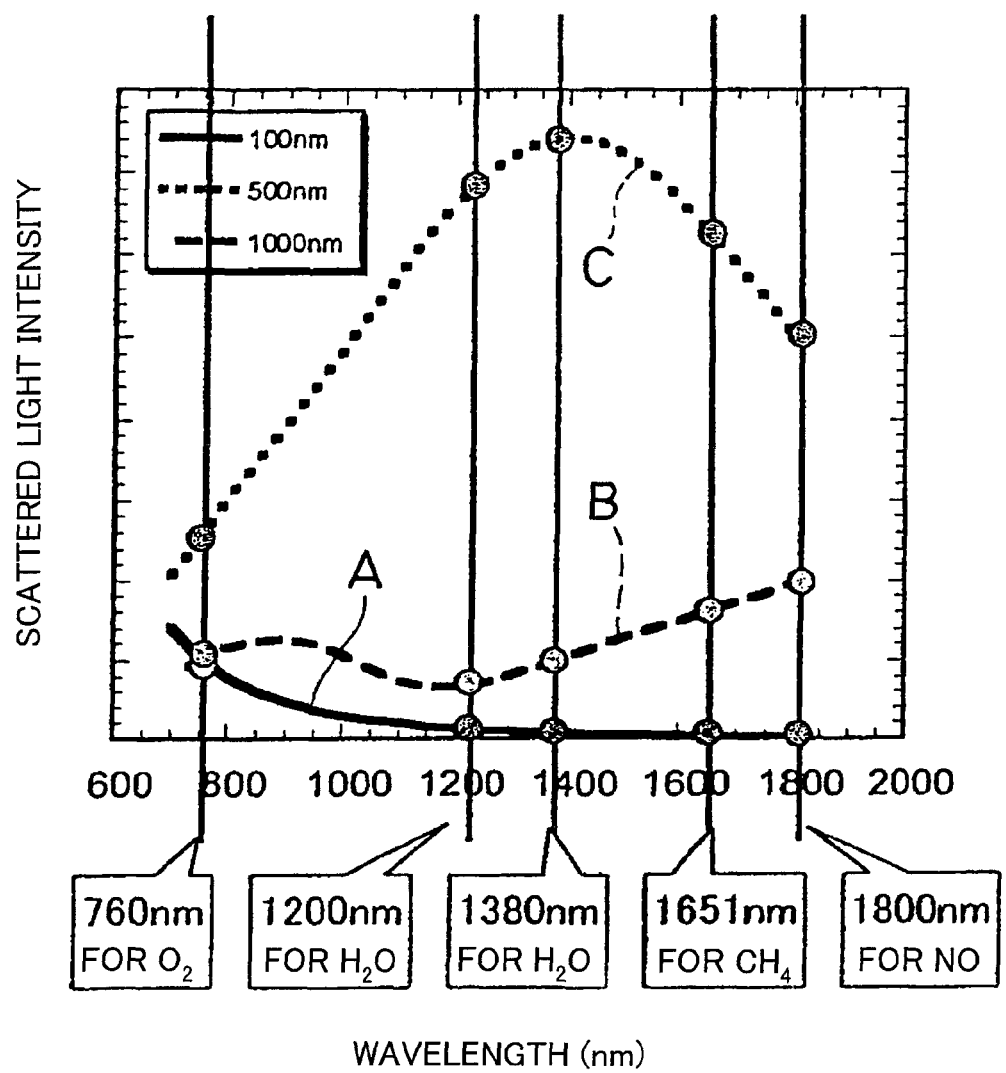

As mentioned above, it is a known fact that when particulate matter PM of the same particle diameter is irradiated with laser light of different wavelengths, the intensity of Mie scattered light generated for each wavelength draws a certain pattern, i.e., pattern data obtained by continuously drawing the intensities of the Mie scattered light generated from the particulate matter PM with respect to the wavelengths will vary depending on the particle diameter of the particulate matter PM. FIG. 6 illustrates one example, where pattern data A shows the case of a particle diameter of 100 nm, pattern data B shows the case of a particle diameter of 1000 nm, and pattern data C shows the case of a particle diameter of 500 nm.

Figure 7:
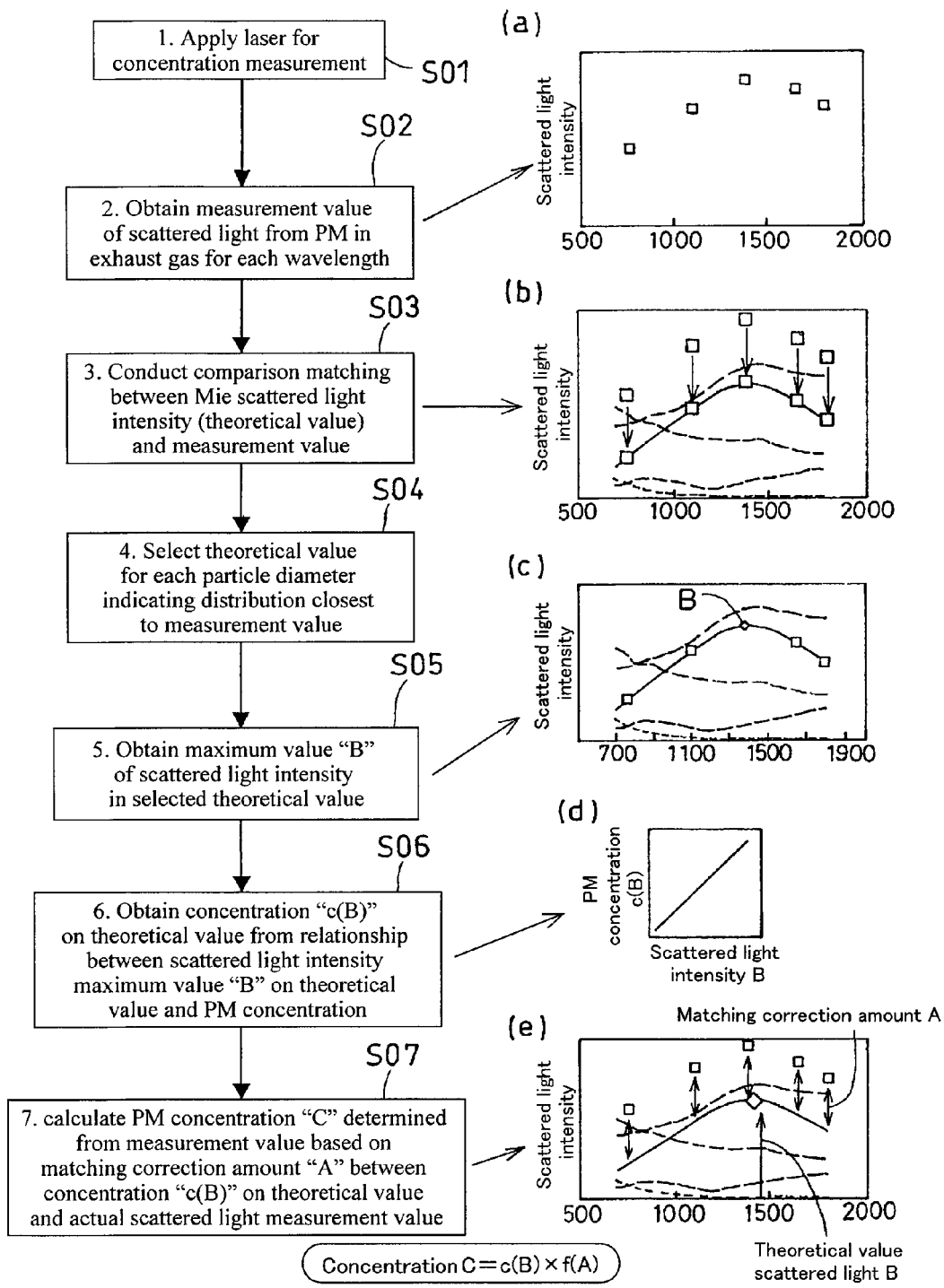
FIG. 7 is a flowchart showing the procedure of an exhaust gas analyzing method according to the present invention.

In FIG. 7, S01 is a laser irradiation step for concentration measurement, in which the above-described laser light of five wavelength bands is applied to the exhaust gas passage hole 21 of the sensor unit 11 (12, 13). At S02, a measurement value (actual measurement value) of the Mie scattered light intensity from the particulate matter PM in the exhaust gas is obtained for each wavelength, and more specifically, the Mie scattered light for each wavelength generated at the sensor unit 11 (12, 13) is detected by the photodetector 71A (71B, 71C) as a scattered light intensity, and the detected signal is converted into an electrical signal. The electrical signal is input as actual measurement data to the personal computer 45 as a signal analyzer. The graph of FIG. 7a illustrates the plotted measurement values of the Mie scattered light intensities measured for five wavelength bands generated by the laser diodes LD1 to LD5 so as to form a pattern, where the horizontal axis represents a wavelength and the vertical axis represents a scattered light intensity.

The personal computer 45 includes a data storage unit 46 and a calculation unit 47, the data storage unit 46 storing theoretical value data about the Mie scattered light intensity specified for each particle diameter. At S03, the calculation unit 47 of the personal computer 45 conducts comparison matching between the stored theoretical value pattern data about the Mie scattered light intensities and the actual measurement value pattern data obtained by the measurement. FIG. 7b describes a method for the pattern matching. Since the data storage unit 46 stores a large number of kinds of pattern data based on theoretical values of the Mie scattered light intensity distribution for each particle diameter as shown in FIG. 6, and the calculation unit 47 conducts the matching of the pattern data obtained by the measurement with the theoretical value pattern data that is the most analogous thereto. Then, at S04, the theoretical value pattern data indicating the distribution that is the closest to the measurement value pattern is selected.

As a result of the pattern matching at S04, the particle diameter of dominant substance making up the particulate matter PM contained in the measured exhaust gas can be estimated with accuracy.

Next, at S5, the maximum value B of the Mie scattered light intensity in the thus selected theoretical value pattern data is obtained (see FIG. 7c). Then, at S06, the calculation unit 47 calculates the particle concentration c(B) as a theoretical value from the relationship between the Mie scattered light intensity maximum value B as a theoretical value and the particle concentration based on the Mie scattering theory. FIG. 7d is a graph illustrating the correlation between the Mie scattered light intensity maximum value B and the particle concentration c(B), which shows substantially linear correlation therebetween.

Finally, at S07, as shown in FIG. 7e, based on a matching correction amount (A) between the particle concentration c(B) as a theoretical value and the scattered light measurement value obtained by the actual measurement, a concentration C (for example, mg/m$^3$ or %) of the particulate matter PM is calculated, which is determined based on a calculation value. Alternatively, based on a coefficient f(A) determined beforehand, the particle concentration c(B) as a theoretical value is calculated for correction, and the actual concentration C of the particulate matter PM is obtained from the following equation (2):

$$\text{Concentration } C = \text{particle concentration } c(B) \times f(A) \qquad (2).$$

When the distribution of the scattered light intensities for each particle is determined theoretically, the distribution of the actual measurement values in the broken line or the solid line of FIG. 7b is compared with the "shape" of the distribution of the theoretical values, and the matching is conducted with the shape as the closest one. As for the maximum value B of the theoretical values with which the matching is conducted, when the actual value for the wavelength corresponding to the determined B (horizontal axis of FIGS. 7a to d) is X, then X/B is the matching correction value (A).

In this way, according to the exhaust gas analyzer of the present embodiment, the concentration, the temperature and the like of a component contained in the exhaust gas can be measured for analysis by irradiating the exhaust gas with laser light. At that time, the Mie scattered light S generated from particulate matter PM contained in the exhaust gas by the irradiation with the laser light is received, whereby the concentration of the particulate matter PM can be calculated concurrently with the analysis of the concentration or the like of a component contained in the exhaust gas. Moreover, the concentration of the particulate matter can be calculated in real time with less computing power.

Figure 8:
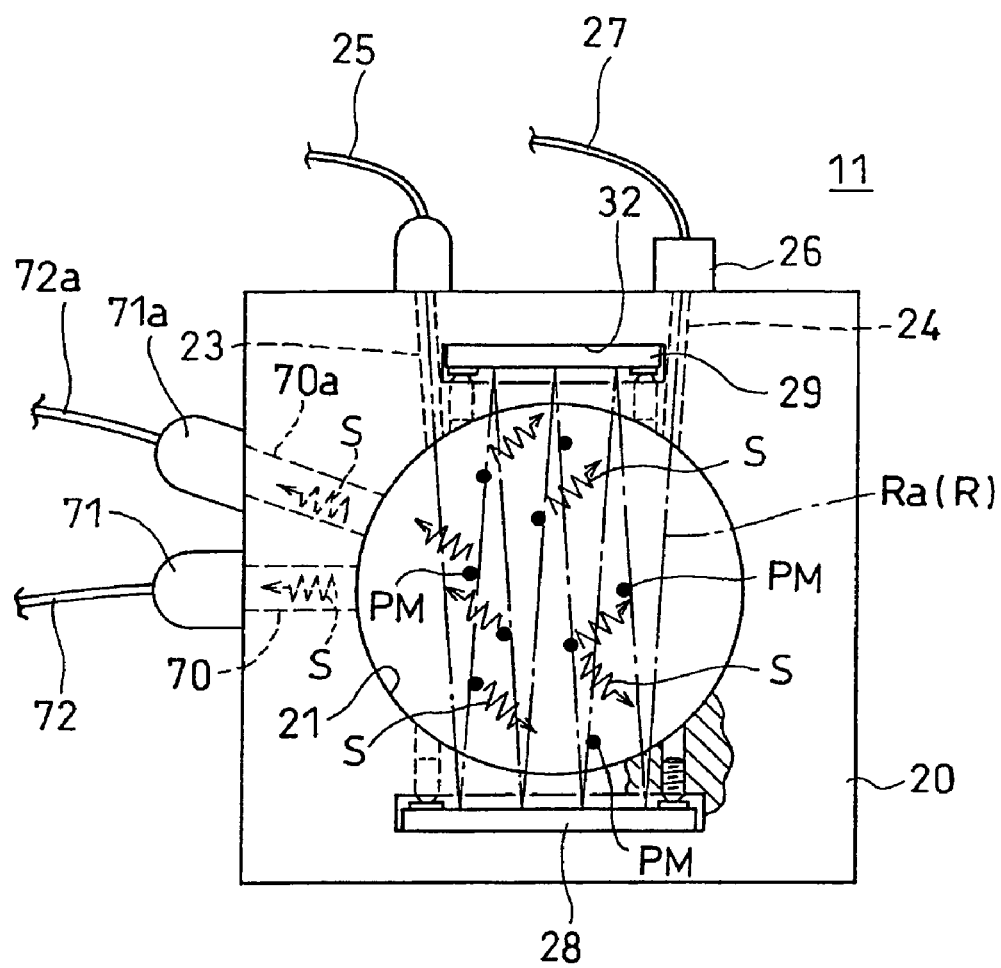
FIG. 8 illustrates another configuration of the sensor unit.

FIG. 8 illustrates another exemplary sensor unit 11. In this example, another third sensor hole 70a is formed in the sensor base 20 so as to be inclined at an appropriate angle (e.g., 20 degrees) with reference to the third sensor hole 70, at which another photodetector 71a is mounted in a similar manner. A signal received by the photodetector 71a is sent via a signal line 72a to the personal computer 45, and the personal computer 45 calculates and compares the signal with a signal received from the photodetector 71, and the measurement value pattern of FIG. 7a is calculated based on the average of these values. In this way, the Mie scattered light intensities are measured by two or more photodetectors 71, whereby the concentration can be measured with higher accuracy.

The invention claimed is:

1. An exhaust gas analyzer that analyzes exhaust gas emitted from an internal combustion by irradiating the exhaust gas with laser light, comprising:
   an exhaust tube through which the exhaust gas is introduced;
   a light irradiation unit disposed in the exhaust tube that applies the laser light in a direction perpendicular to a direction of extension of the exhaust tube at a position of the exhaust tube where the light irradiation unit is disposed;
   a reflecting device configured to reflect the laser light a plurality of times such that reflected laser light generates Mie scattered light from particulate matter contained in the exhaust gas by irradiating the particulate matter with the reflected laser light;
   a transmitted light photoreceiving unit that receives the laser light that has passed through the exhaust gas;
   a scattered light photoreceiving unit that receives the generated Mie scattered light; and
   a calculation unit that calculates a concentration of a component in the exhaust gas based on photoreceiving data of a transmitted light intensity obtained from the transmitted light photoreceiving unit, and calculates a concentration of the particulate matter contained in the exhaust gas based on actual measurement data of a scattered light intensity obtained by the scattered light photoreceiving unit.

2. The exhaust gas analyzer according to claim 1, wherein the calculation unit comprises a data storage unit that stores theoretical value data about a Mie scattered light intensity specified for each particle diameter, and the calculation unit calculates the concentration of the particulate matter contained in the exhaust gas based on the actual measurement data of a Mie scattered light intensity obtained by the scattered light photoreceiving unit and the theoretical value data stored in the data storage unit and is specified for each particle diameter.

3. The exhaust gas analyzer according to claim 2, comprising a plurality of the scattered light photoreceiving units, wherein the calculation unit further comprises means that calculates an average of actual measurement data of Mie scattered light intensities obtained by the plurality of scattered light photoreceiving units.

4. A method for analyzing exhaust gas emitted from an internal combustion by irradiating laser light into an exhaust tube though which the exhaust gas is introduced, the method comprising the steps of:
   irradiating the exhaust gas with the laser light in a direction perpendicular to a direction of extension of the exhaust tube at a position of the exhaust tube where the laser light is irradiated, reflecting the laser light a plurality of times with a reflecting device such that reflected laser light generates Mie scattered light from particulate matter contained in the exhaust gas by irradiating the particulate matter with the reflected laser light, receiving the laser light that has passed through the exhaust gas, and calculating a concentration of a component contained in the exhaust gas based on the received laser light; and
   receiving the generated Mie scattered light, and calculating a concentration of the particulate matter based on actual measurement data of an intensity of the received Mie scattered light.

5. The method for analyzing exhaust gas according to claim 4,
   wherein the concentration of the particulate matter is calculated based on the actual measurement data of the Mie scattered light intensity and theoretical value data about a Mie scattered light intensity specified for each particle diameter.

6. The method for analyzing exhaust gas according to claim 5,
   wherein the concentration of the particulate matter is calculated using pattern data including actual measurement data of Mie scattered light intensities from the particulate matter contained in the exhaust gas, the actual measurement data being continuous with respect to wavelengths,
   the method including the steps of:
   comparing the pattern data on the actually measured Mie scattered light intensities and theoretical value pattern data about Mie scattered light intensity specified for each particle diameter so as to select theoretical value pattern data analogous to the pattern data on the actually measured Mie scattered light intensities,
   acquiring a maximum value in the selected theoretical value pattern data and calculating a theoretical value concentration of the particulate matter as theoretical value data based on the acquired value, and
   correcting the calculated theoretical value concentration of the particulate matter with a measurement value of the Mie scattered light intensity that is actually measured to calculate an actual particulate matter concentration.

7. The exhaust gas analyzer according to claim 1,
   wherein the reflecting device comprises a pair of mirrors disposed at opposing positions with an exhaust gas passage being sandwiched therebetween.

8. The method for analyzing exhaust gas according to claim 4,
   wherein the reflecting further comprises reflecting the laser light from a pair of mirrors disposed at opposing positions with an exhaust gas passage being sandwiched therebetween.

* * * * *